United States Patent [19]

Yamabe et al.

[11] 4,153,804
[45] May 8, 1979

[54] PROCESS FOR PRODUCING FLUORINATED VINYL ETHER HAVING ESTER GROUP

[75] Inventors: Masaaki Yamabe, Machida; Seiji Munekata, Yokohama; Shunichi Samejima, Tokyo, all of Japan

[73] Assignee: Asahi Glass Co. Ltd., Tokyo, Japan

[21] Appl. No.: 917,637

[22] Filed: Jun. 21, 1978

Related U.S. Application Data

[63] Continuation-in-part of Ser. No. 765,609, Feb. 4, 1977, abandoned.

[51] Int. Cl.$^2$ .............................................. C07C 69/65
[52] U.S. Cl. .................................... 560/183; 560/184; 560/185; 560/219; 526/245; 562/586
[58] Field of Search ............... 560/183, 184, 185, 219; 260/535 H; 562/586

[56] References Cited

U.S. PATENT DOCUMENTS

| | | | |
|---|---|---|---|
| 2,839,513 | 6/1958 | Ahlbrecht et al. | 560/184 |
| 3,250,808 | 5/1966 | Moore, Jr. et al | 560/184 |

*Primary Examiner*—James O. Thomas, Jr.
*Assistant Examiner*—Leah Hendriksen
*Attorney, Agent, or Firm*—Oblon, Fisher, Spivak, McClelland & Maier

[57] ABSTRACT

A fluorinated vinyl ether having an ester group which has the formula $$CF_2=CFOCF_2(CF(CF_3)OCF_2)_{n-1}(Rf)_m CO_2R$$

wherein n represents an integer of 1 to 5; m represents 0 or 1; Rf represents a $C_1$–$C_{10}$ bifunctional perfluoro group and R represents an alkyl group, is produced by reacting fluorinated acyl fluoride having an ester group which has the formula $$FOC(CF(CF_3)OCF_2)_n(Rf)_m CO_2R$$

with an alkali metal carbonate to produce an alkali metal salt of fluorinated carboxylic acid having an ester group which has the formula $$MOOC(CF(CF_3)OCF_2)_n(Rf)_m CO_2R$$

wherein M represnts an alkali metal;
and then, thermally decomposing the alkali metal salt of fluorinated carboxylic acid having an ester group.

8 Claims, No Drawings

PROCESS FOR PRODUCING FLUORINATED VINYL ETHER HAVING ESTER GROUP

REFERENCE TO RELATED APPLICATIONS

This application is a continuation-in-part application of application Ser. No. 765,609, filed Feb. 4, 1977, now abandoned.

BACKGROUND OF THE INVENTION

1. Field of the Invention

The present invention relates to a process for producing a fluorinated vinyl ether having an ester group which has the formula

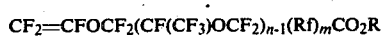
$CF_2=CFOCF_2(CF(CF_3)OCF_2)_{n-1}(Rf)_m CO_2R$ wherein n represents an integer of 1 to 5; m represents 0 or 1; RF represents a $C_1-C_{10}$ bifunctional perfluoro group and R represents an alkyl group.

2. Description of the Prior Art

The fluorinated vinyl ethers are useful as monomers for producing fluorinated polymers. The fluorinated vinyl ethers obtained by the process of the invention can be used as comonomers for forming cure-sites in fluorinated polymers and as monomers for producing fluorinated polymers having special functions, and can be used in various fields.

The processes for producing the fluorinated vinyl ethers having an ester group are disclosed in Japanese Patent publication No. 22327/1970 and British Pat. No. 1,145,445.

The conventional processes include the reaction of perfluoro diacyl fluoride with hexafluoropropylene oxide to produce perfluoro [2-methyl-3-Oxa-alkane] diacyl fluorides. In the second step, the diacyl fluoride is esterified with an alcohol preferably with methanol to produce the diester. The diester is then either saponified with an anhydrous methanol solution of potassium, sodium or cesium hydroxide to give the di-metal salt, or converted by a reaction with water to the diacid which is then neutralized with an aqueous solution of one of the above hydroxides. Then, the di-metal salt is converted by a thermal decomposition, to the mono-metal salt and the resulting mono-metal salt is hydrolyzed to give the fluorinated vinyl ether carboxylic acid and then the product is converted by an esterification to give the fluorinated vinyl ether having an ester group.

In the conventional processes, many reaction steps are required and the yield in the thermal decomposition of the di-metal salt of perfluorodicarboxylic acid is remarkably low such as about 25%. In order to apply the conventional process in industrial scale, many difficult operations are required.

It has not been known to produce fluorinated vinyl ethers having an ester group in an industrial scale in high efficiency.

The inventors have studied to produce the fluorinated vinyl ethers having an ester group in high yield through a less complicated process.

As the result, the following important facts have been found.

The fluorinated compounds having

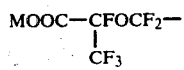
$$MOOC-\underset{\underset{CF_3}{|}}{C}FOCF_2-$$

group at one end and an ester group of $-CO_2R$ at the other end could be thermally decomposed at relatively low temperature whereby

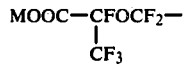
$$MOOC-\underset{\underset{CF_3}{|}}{C}FOCF_2-$$

group is surprisingly converted to the fluorinated vinyl ether group ($CF_2=CFOCF_2-$) without modifying the ester group, and the fluorinated vinyl ether having an ester group could be obtained in high yield.

It has hither to been known that when fluorocarbonyl group ($-COF$) or an ester group ($-CO_2R$) is treated with an alkali metal hydroxide, they are converted to an alkali metal salt of carboxylic acid ($-COOM$). So, when a fluorinated acid fluoride having an ester group ($FOC-A-CO_2R$ wherein A represents bifunctional perfluoro group) is treated with an alkali metal hydroxide, it is converted to the di-metal salt ($MOOC-A-COOM$).

On the other hand, it has been found that when a fluorinated acid fluoride having an ester group ($FOC-A-CO_2R$ wherein A represents bifunctional perfluoro group) is treated with an alkali metal carbonate, only $-COF$ group is surprisingly converted to $-COOM$ group without any affection to $-CO_2R$ group.

It has been found that the acid fluoride having the formula

$FOC(CF(CF_3)OCF_2)_n(Rf)_m CO_2R$ could be converted to an alkali metal salt of fluorinated carboxylic acid having an ester group which has the formula

$MOOC(CF(CF_3)OCF_2)_n(Rf)_m CO_2R$ in high yield by the reaction with an alkali metal carbonate.

While the conventional process, which gives the fluorinated vinyl ethers having an ester group, required many reaction steps, pyrolyzing the alkali metal salts of fluorinated carboxylic acids having an ester group provides a more simpler way of production.

SUMMARY OF THE INVENTION

It is an object of the present invention to provide a process for producing a fluorinated vinyl ether having an ester group in high yield through a less complicated operation, which could be adopted industrially.

The object of the present invention has been attained by providing a process for producing a fluorinated vinyl ether having an ester group which has the formula

$CF_2=CFOCF_2(CF(CF_3)OCF_2)_{n-1}(Rf)_m CO_2R$ wherein n represents an integer of 1 to 5; m represents 0 or 1; Rf represents a $C_1-C_{10}$ bifunctional perfluoro group and R represents an alkyl group which comprises reacting a fluorinated acid fluoride having an ester group which has the formula

$FOC(CF(CF_3)OCF_2)_n(Rf)_m CO_2R$ with an alkali metal carbonate to produce an alkali metal salt of fluorinated carboxylic acid having an ester group which has the formula MOOC(CF(CF₃)OCF₂)ₙ(Rf)ₘCO₂R wherein M represents an alkali metal, and then, thermally decomposing the alkali metal salt of fluorinated carboxylic acid having an ester group.

DETAILED DESCRIPTION OF THE PREFERRED EMBODIMENTS

In accordance with the process of the present invention, the reaction steps can be remarkably reduced and the yield of the pyrolytic reaction reaches as high as 70% or more, in comparison with the conventional processes including the thermal decomposition of the di-metal salt. Accordingly, the object compounds of fluorinated vinyl ethers having an ester group can be obtained in high yield without the complicated process having many reaction steps.

In the pyrolytic reaction of the present invention, the alkali metal salt as the starting material is solid and the object compound of the fluorinated vinyl ether can be collected in gaseous state. Accordingly, the reaction operation and the separation operation are advantageous in comparison with those of the conventional process. Moreover, the yield in the reaction of the fluorinated acyl fluoride with the alkali metal carbonate can be remarkably high such as higher than 90%.

The fluorinated acyl fluoride having the formula

FOC(CF(CF₃)OCF₂)ₙ(Rf)ₘCO₂R which is used as the starting material, can be easily obtained by reacting a fluorinated acyl fluoride having the formula FOC(Rf)ₘCO₂R with hexafluoropropylene oxide in the presence of a catalyst of an alkali metal fluoride.

That is, the fluorinated acid fluoride having an ester group which has the formula FOC(CF(CF₃)OCF₂)ₙ(Rf)ₘCO₂R can be obtained as the adduct of n moles of hexafluoropropylene oxide. In the formula, n is usually an integer of 1 to 5 especially 1 to 2, and Rf is a C₁–C₁₀ bifunctional perfluoro group which can be straight chain or branched chain having one or more ether bond. It is preferable that m=1 and Rf is a C₁–C₅ bifunctional perfluoro group (—(CF₂)₁₋₅—).

In the formula, R is an alkyl group such as a C₁–C₁₀ alkyl group especially a C₁–C₅ alkyl group.

The fluorinated acyl fluorides having the formula

FOC(Rf)ₘCO₂R can be produced by the reaction of a perfluorolactone with an alcohol which is disclosed in the former patent applications (U.S. Ser. No. 739,727; British Application No. 44890/1976; W. German Application No. P. 2651531. 1; French application No. 7,633,945 and Italian application No. 29231/1976).

The fluorinated acyl fluoride esters can be produced by reacting the following specific perfluorolactone with an alcohol in the following reaction.

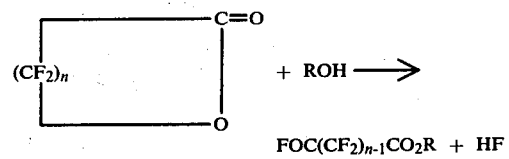

FOC(CF₂)ₙ₋₁CO₂R + HF wherein n represents an integer from 2 to 4 and R represents an alcohol residual group.

The perfluorolactones used in the process of the invention can be produced by the reaction disclosed in allowed U.S. patent application Ser. No. 711,978, now U.S. Pat. No. 4,116,977, issued Sept. 26, 1978.

That is, the perfluorolactone can be produced by reacting an α,ω-diiodoperfluoroalkane or a perfluoroacyl halide having a terminal iodo group with fuming sulfuric acid.

It is also possible to produce the perfluorolactone by heating a silver salt of perfluoroglutarate in the presence of iodine by the method of R. E. Banks, et al., (JCS(C), 1967, 2333).

The alcohols used as the other starting material can be various alcohols.

Suitable alcohols include alcohols having 1 to 8 carbon atoms. In the formula ROH, R can be an alkyl group having 1 to 8 carbon atoms, a straight chain or a branched chain aralkyl group, or an aryl group, which can have an inert substituent.

The reaction of the perfluorolactone with the alcohol in the process of the invention can be carried out by diluting the starting material with an inert organic solvent.

Suitable inert organic solvents include hydrocarbon nitriles having 2 to 12 carbon atoms such as propionitrile, benzonitrile, acetonitrile; aliphatic polyethers and alicyclic ethers having 4 to 16 carbon atoms such as ethyleneglycol dimethyl ether, diethyleneglycol dimethyl ether, dioxane and other polar solvents. It is also possible to use chlorofluoroalkane such as trichloromonofluoromethane and trichlorotrifluoroethane and other haloalkanes.

The reaction temperature can be selected. Since the exothermic reaction of the perfluorolactone with the alcohol causes heat, it is preferable to react them at −80° to +100° C. preferably −40° to +50° C. especially −60° C. to +70° C. in order to react them under controlled conditions.

In the process of the present invention, the reaction of the fluorinated acyl fluoride having an ester group FOC(CF(CF₃)OCF₂)ₙ(Rf)ₘCO₂R with an alkali metal carbonate is carried out as the first step.

Suitable alkali metal carbonates include carbonates of lithium, potassium, cesium and sodium. It is preferable to use potassium carbonate or sodium carbonate.

Suitable fluorinated acyl fluorides having an ester group include
FOCCF(CF₃)OCF₂CF₂CF₂CO₂C₂H₅,
FOCCF(CF₃)OCF₂CF₂CF₂CO₂CH₃,
FOC(CF(CF₃)OCF₂)₂CF₂CF₂CO₂C₂H₅,
FOC(CF(CF₃)OCF₂)₂CF₂CF₂CO₂CH₃,
FOC(CF(CF₃)OCF₂)₂CF₂CF₂CF₂CO₂C₂H₅,
FOC(CF(CF₃)OCF₂)₂CF₂CF₂CF₂CO₂CH₃
FOCCF(CF₃)OCF₂CF₂CF₂CF₂CO₂CH₃, FOCCF(CF$_3$)OCF$_2$CF$_2$CF$_2$CF$_2$CF$_2$CO$_2$C$_2$H$_5$ etc.

In the process of the invention, it is also possible to combine two or more fluorinated acyl fluorides having an ester (starting material) which have different n, m, Rf or R in the formula.

For example, it is possible to react two types of the fluorinated acyl fluorides (n=1 and n=2) with an alkali metal carbonate to produce MOOCCF(CF$_3$)OCF$_2$RfCO$_2$R and MOOC(CF(CF$_3$)OCF$_2$)$_2$RfCO$_2$R. It is also possible to combine two or more alkali metal carbonates.

The reaction of the fluorinated acyl fluoride with the alkali metal carbonate in the first step can be carried out with or without a solvent.

Suitable solvents include hydrocarbons such as hexane, heptane; halohydrocarbons such as chloroform, carbon tetrachloride, perchloroethylene; ethers such as tetrahydrofuran, mono-, di-, tri- or tetra-ethyleneglycol dimethyl ethers which are inert to —COF group.

The reaction temperature is usually in a range of $-30°$ C. to $+160°$ C. preferably $10°$ C. to $130°$ C.

The amount of the alkali metal carbonate is usually more than 1 mole preferably about 1 to 2 mole per 1 mole of the fluorinated acyl fluoride.

When the temperature is too high, the decomposition of the resulting alkali metal salt of fluorinated carboxylic acid may be induced. When the temperature is too low, the reaction velocity is too slow.

As the operation in the first step, a dried alkali metal carbonate and if necessary, a substantial anhydrous solvent is charged in the reactor and the fluorinated acyl fluoride is added dropwise to it with stirring at a predetermined temperature. It is also possible to charge the fluorinated acyl fluoride and the alkali metal carbonate in the reactor and then to react them at a predetermined temperature for a predetermined time. Usually, after the reaction completed, the solvents and the unreacted starting materials are evacuated under a reduced pressure, and the solid reaction products are obtained.

The reaction time is usually from 1 to 30 hours preferably from 3 to 20 hours.

Thus, the alkali metal salt of fluorinated carboxylic acid having an ester group which has the formula MOOC(CF(CF$_3$)OCF$_2$)$_n$(Rf)$_m$CO$_2$R is obtained as the product in the first step almost quantitatively.

The alkali metal salt is converted to the object compound of fluorinated vinyl ether having an ester group by the pyrolysis in the second step.

The alkali metal salt of fluorinated carboxylic acid having an ester group could be separated and then pyrolyzed. In the process of the invention, it is possible to use the mixture of reaction product in the first step, containing as a by-product an alkali metal fluoride and the unreacted alkali metal carbonate, for the pyrolysis in the second step without separating the alkali metal salt.

The conversion of the alkali metal salt to the fluorinated vinyl ether having an ester group in the second step can be easily accomplished by the pyrolysis of the solid alkali metal salt at a predetermined temperature.

The reactor for the pyrolysis can be made of various materials such as glass, stainless steel, nickel, Hastelloy etc.

The temperature in the thermal decomposition is usually in a range of 100 to 350° C. preferably 140 to 300° C. The thermal decomposition can be carried out under a super atmospheric pressure, the atmospheric pressure or a reduced pressure. However, in order to remove the by-product of CO$_2$ out of the reaction system, it is preferable to carry out under a reduced pressure, such as less than 100mmHg preferably less than 50mmHg.

When the temperature is too high, the selectivity for the object compound is reduced. When the temperature is too low, the conversion of the starting material is reduced.

In usual, it is preferable to rapidly distill the object compound out of the reaction system.

The pyrolysis can be carried out in an organic solvent.

Suitable solvents include ethyleneglycol dimethyl ethers such as diethyleneglycol dimethyl ether, triethyleneglycol dimethyl ether, tetraethyleneglycol dimethyl ether; N-methyl pyrrolidone, dimethylsulfoxide, hydrocarbon nitriles, N,N-dialkylamides etc. which are polar solvents.

It is possible to carry the fluorinated vinyl ether with an inert gas by feeding the inert gas in the thermal decomposition zone.

In this procedure, it is preferable to carry out the pyrolysis in the absence of a proton source such as water, because a disadvantageous side-reaction which is not negligible, is caused in the presence of a proton source.

In the pyrolysis, the alkali metal salt as the starting material is charged in an apparatus equipped with a stirrer and a heating jacket under reduced pressure. The products are collected through a series of traps set between the apparatus and the vacuum pump, a trap maintained at $-78°$ C. which is used for collecting the object compound and a trap maintained at $-196°$ C. The pyrolysis is carried out at a predetermined temperature under a predetermined pressure for from 1 to 30 hours preferably 1 to 15 hours. It is the optimum to gradually charge the alkali metal salt into the reactor which is maintained at predetermined temperature whereby the pyrolysis is resulted. The product was collected in the trap maintained at $-78°$ C. and the product was distilled under a reduced pressure to obtain the object compound of fluorinated vinyl ether having an ester group.

The object compound produced by the pyrolysis which is distilled out of the reaction system under a reduced pressure, can be collected in a trap. The object compound remained in the reaction system can be separated by washing the reaction mixture with water etc.

The fluorinated vinyl ethers obtained by the process of the present invention can be used to produce useful vulcanizable plastics and elastomers by copolymerizing the fluorinated vinyl ether with the other fluorinated monomer such as vinylidene fluoride, hexafluoropropylene, tetrafluoroethylene and perfluoro(alkyl vinyl ether). For example, the fluorinated vinyl ethers can be readily employed as cure-site monomers in fluorinated type polymer systems as disclosed in U.S. Pat. No. 3,546,186.

The fluorinated vinyl ethers of the present invention have ester functional group whereby they are useful as the monomers for preparing fluorinated cation exchange membranes. For example, the fluorinated ether of CF$_2$=CFO(CF$_2$)$_3$CO$_2$CH$_3$ or CF$_2$=CFOCF$_2$CF(CF$_3$)O(CF$_2$)$_3$CO$_2$CH$_3$ is copolymerized with a fluorinated olefin of tetrafluoroethylene or trifluorochloroethylene and the resulting copolymer is fabricated to a film having a thickness of 100 to 500μ and hydrolyzed it to prepare the cation exchange membrane. The copolymer having 2 to 40 mole % of the fluorinated vinyl ether component of the present invention is useful as the cation exchange membrane as disclosed in U.S. Pat. No. 4,065,366.

The invention will be further illustrated by certain specific examples which are included for purposes of illustration only and not intended to be limiting unless otherwise specified.

REFERENCE 1

Preparation of 6-carboethoxy-perfluoro-2-methyl-3-oxa-hexanoyl fluoride

In a 1 liter autoclave equipped with a stirrer, 17.7 g (0.116 mole) of anhydrous cesium fluoride powder, 188 g of tetraethyleneglycol dimethyl ether and 240 g (1.09 mole) of 3-carboethoxy-perfluoropropionyl fluoride having the formula $$FOC(CF_2)_2CO_2CH_2CH_3$$

were charged. The mixture was vigorously stirred at a reaction temperature of $-10°$ C. to $0°$ C. under a pressure of less than 1 kg/cm$^2$, and 211 g (1.27 mole) of hexafluoropropylene oxide was added continuously for 3 hours.

After the reaction, the reaction mixture was distilled to obtain 240 g of the object compound of 6-carboethoxy-perfluoro-2-methyl-3-oxa-hexanoyl fluoride having the formula $$\underset{\underset{CF_3}{|}}{FOCCFO}(CF_2)_3CO_2CH_2CH_3$$

(boiling point: about 53° C./15mmHg)(yield: 57%) and to recover 44 g of the starting material of 3-carboethoxy-perfluoropropionyl fluoride.

REFERENCE 2

Preparation of 9-carboethoxy-perfluoro-2,5-dimethyl-3,6-dioxa-nonanoyl fluoride

In a 1 liter autoclave equipped with a stirrer, 7.6 g (0.05 mole) of anhydrous cesium fluoride powder, 42 g of tetraethyleneglycol dimethyl ether and 220 g (1.0 mole) of 3-carboethoxy-perfluoropropionyl fluoride having the formula $$FOC(CF_2)_2CO_2CH_2CH_3$$

were charged. The mixture was vigorously stirred at a reaction temperature of $-10°$ C. to $0°$ C. under a pressure of about 1 kg/cm$^2$, 380 g (2.2 mole) of hexafluoropropylene oxide was added continuously for 6 hours.

After the reaction, the reaction mixture was distilled to obtain 309 g of the object compound of 9-carboethoxy-perfluoro-2,5-dimethyl-3,6-dioxa-nonanoyl fluoride (boiling point:about 66° C./8mmHg)(yield:56%).

REFERENCE 3

Preparation of 6-carbomethoxy-perfluoro-2-methyl-3-oxa-hexanoyl fluoride

In a 1 liter autoclave equipped with a stirrer, 15.2 g (0.1 mole) of anhydrous cesium fluoride powder, 70 cc of diethyleneglycol dimethyl ether, 206 g (1.0 mole) of 3-carbomethoxy-perfluoropropionyl fluoride having the formula $$FOC(CF_2)_2CO_2CH_3$$

were charged. The mixture was vigorously stirred at a reaction temperature of $-20°$ C. to $-10°$ C. under a pressure of less than 1 kg/cm$^2$, and 186 g (1.12 mole) of hexafluoropropylene oxide was added continuously for 4 hours.

After the reaction, the reaction mixture was distilled to obtain 208 g of the object compound of 6-carbomethoxy-perfluoro-2-methyl-3-oxa-hexanoyl fluoride having the formula $$\underset{\underset{CF_3}{|}}{FOCCFO}(CF_2)_3CO_2CH_3$$

(boiling point: 68° C./65mmHg)(yield: 56%) and to recover 39 g of 3-carbomethoxy-perfluoropropionyl fluoride.

REFERENCE 4

Preparation of 8-carbomethoxy-perfluoro-2-methyl-3-oxa-octanoyl fluoride

In a 1 liter autoclave equipped with a stirrer, 15.2 g (0.1 mole) of anhydrous cesium fluoride powder, 60 cc of diethyleneglycol dimethyl ether and 306 g (1.0 mole) of 5-carbomethoxy-perfluoropentanoyl fluoride having the formula $$FOC(CF_2)_4CO_2CH_3$$

were charged. The mixture was vigorously stirred at a reaction temperature of 0° to 10° C. under a pressure of less than 2 kg/cm$^2$, and 186 g (1.12 mole) of hexafluoropropylene oxide was added continuously for 2.5 hours.

After the reaction, the reaction mixture was distilled to obtain 401 g of the object compound of 8-carbomethoxy-perfluoro-2-methyl-3-oxa-octanoyl fluoride having the formula $$\underset{\underset{CF_3}{|}}{FOCCFO}(CF_2)_5CO_2CH_3$$

(yield: 71%).

EXAMPLE 1

In a 100 ml four necked flask equipped with a reflux condenser, a dropping funnel and a magnetic stirrer which was purged with nitrogen gas, 8.24 g of sodium carbonate dried at 280° C. for 2 hours and 40 ml of anhydrous diethyleneglycol dimethyl ether were charged.

The mixture was stirred and 20.0 g of 6-carboethoxy-perfluoro-2-methyl-3-oxa-hexanoyl fluoride of Reference 1 was added dropwise at room temperature during 3 hours.

After the addition, the stirring was continued for further 1 hour and the solvent of diethyleneglycol dimethyl ether was distilled off. The residue was dried at 80° C./3mmHg for 2 hours to obtain 25.2 g of a solid mixture of the object compound having the formula

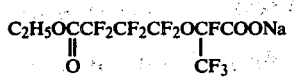

and sodium fluoride and sodium carbonate.

According to the analysis, the amount of the object compound was 20.3 g and the yield was 97%.

EXAMPLE 2

In 1 liter glass autoclave which was purged with nitrogen gas, 125 g of potassium carbonate dried at 180° C. for 2 hours, 500 ml of n-heptane which was predried with metallic sodium and 233 g of 6-carboethoxy-perfluoro-2-methyl-3-oxa-hexanoyl fluoride were charged and the mixture was stirred to react at 90° C. for 10 hours.

After the reaction, n-heptane was distilled off at 50° C./130mmHg and the residue was dried at 70° to 80° C./3mmHg for 2 hours to obtain 326 g of a solid mixture of the object compound having the formula

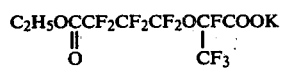

and potassium fluoride and potassium carbonate.

According to the analysis, the yield of the object compound was 98%.

EXAMPLE 3

In a 100 ml round bottom flask, 21 g of the solid object compound of Example 1 was charged. The flask was connected to a series of traps, a trap maintained at −78° C. and a trap maintained at −196° C., followed by a vacuum pump. The reaction was carried out at a reaction temperature of 170° C. under a reduced pressure of 3mmHg for 3 hours with stirring.

In the trap maintained at −78° C., 14.9 g of a liquid was collected. The liquid was carefully distilled, and 10.1 g of ethyl perfluoro-5-oxa-6-heptenoate was obtained.

EXAMPLE 4

In the apparatus of Example 3, 23.0 g of the solid mixture of the object compound, potassium fluoride and potassium carbonate of which was obtained by the reaction of 17.0 g of the starting material and 8.3 g of potassium carbonate, was charged, and the reaction was carried out at 150° to 155° C. under a reduced pressure of 2 to 4 mmHg for 3 hours with stirring.

In the trap maintained at −78° C., 13.3 g of a liquid was collected.

The liquid was distilled in accordance with the process of Example 3 and 9.2 g of ethyl perfluoro-5-oxa-6-heptenoate was obtained.

EXAMPLE 5

In the apparatus of Example 3, 46.5 g of the solid mixture of

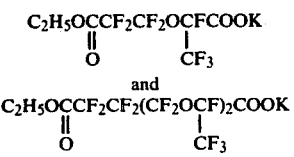

and potassium fluoride and potassium carbonate which was produced by reacting a mixed acid fluorides of

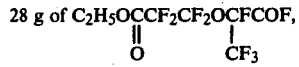

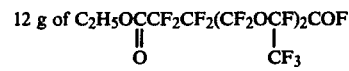

with 19.5 g of potassium carbonate, was charged.

The reaction was carried out at a reaction temperature of 155° to 160° C. under a reduced pressure of 2 mmHg for 5 hours with stirring.

In the trap maintained at −78° C., 30.2 g of a liquid was collected.

The liquid was carefully distilled, and 14.6 g of ethyl perfluoro-5-oxa-6-heptenoate and 5.4 g of ethyl perfluoro-5,8-dioxa-6-methyl-9-decenoate were obtained.

EXAMPLE 6

In a 5 liter reactor equipped with a reflux condenser and a stirrer, 740 g of anhydrous potassium carbonate, 3 liters of perchloroethylene and 930 g of FOCCF(CF$_3$)O(CF$_2$)$_3$CO$_2$CH$_3$ were charged and the reaction was carried out at the reaction temperature of 100° to 105° C. for 5.5 hours with vigorously stirring until ceasing carbon dioxide gas.

After the reaction, the solid component was separated by a filtration and was dried to obtain 1531 g of a mixture of the potassium salt of carboxylic acid having an ester group and KF and K$_2$CO$_3$. The amount of the potassium salt of carboxylic acid having an ester group in the solid component was 1002 g and the yield was 98%.

In the apparatus of Example 3, pyrolysis of 500 g of the mixture (containing 327 g of the potassium salt of carboxylic acid), was carried out at 230° C. to obtain 203 g of the crude pyrolyzed liquid.

According to the gas chromatography analysis, the content of the object compound of vinyl ether having the formula

in the liquid was 138 g and the reaction yield was 56%.

EXAMPLE 7

In the reactor of Example 6, 3 liters of perchloroethylene, 750 g of anhydrous potassium carbonate and 1350 g of FOCCF(CF$_3$)O(CF$_2$)$_3$CO$_2$CH$_3$ were charged and the reaction was carried out at the reaction temperature of 120° C. for 3.5 hours with vigorously stirring.

After the reaction, 1870 g of the solid component was separated. The amount of the potassium salt of carboxylic acid having an ester group in the solid component was 1420 g and the yield was 96%.

EXAMPLE 8

In a 1 liter reactor equipped with a stirrer, a solid material inlet and a gas outlet, 180 g of anhydrous potassium fluoride was charged and the reactor was heated to 250° C. under the reduced pressure of 3mmHg. A 50 g of the solid component obtained in Example 7 was gradually added through the solid material inlet into the reactor during 2 hours. The pyrolyzed product discharged from the gas outlet was collected in a trap dipped in a dry-ice-acetone bath. The generated carbon dioxide gas was collected in a trap cooled with liquid nitrogen.

The amount of the collected liquid was 26.6 g and the content of the vinyl ether having the formula $$CF_2=CFO(CF_2)_3CO_2CH_3$$

was 21.1 g. The yield to the potassium salt was 74%.

EXAMPLE 9

In a 2 liters reactor equipped with a reflux condenser and a stirrer, 445 g (0.78 mole) of $FOCCF(CF_3)OCF_2CF(CF_3)O(CF_2)_3CO_2C_2H_5$ which was produced in Reference 2, 215 g of anhydrous potassium fluoride and 860 ml of perchloroethylene were charged and the reaction was carried out at the reaction temperature of 100° to 105° C. for 6 hours with vigorously stirring, whereby a solid mixture of the potassium saltof carboxylic acid having an ester and KF and $K_2CO_3$ was obtained. The conversion was 98.6%.

In the reactor of Example 8, all of the solid mixture was charged and the pyrolysis was carried out at 210° to 220° C. for 5.5 hours under the reduced pressure of 2 mmHg. As the result, 349 g of the crude pyrolyzed liquid was collected in a trap maintained at the dry-ice temperature. The content of the object compound of vinyl ether $$CF_2=CFOCF_2CF(CF_3)O(CF_2)_3CO_2C_2H_5$$

was 339 g and the yield in the pyrolysis was 90%. The boiling point of the monomer of the vinyl ether was 85° C./19mmHg.

EXAMPLE 10

In a 500 ml reactor equipped with a reflux condenser and a stirrer, 50 g of anhydrous potassium carbonate, 200 ml of n-heptane and 96 g of $$FOCCF(CF_3)OCF_2CF(CF_3)O(CF_2)CO_2CH_3$$

were charged and the reaction was carried out at the reaction temperature of 91° to 95° C. for 8 hours with vigorously stirring. After the reaction, the reaction mixture was filtered and was dried to obtain 134 g of white solid component.

According to the analysis, the solid component contained 100 g of the potassium salt of carboxylic acid. The conversion was 97%.

In the reactor of Example 8, all of the solid component was charged and the pyrolysis was carried out at 200° to 210° C. for 3.5 hours under the reduced pressure of 4mmHg. As the result, 70 g of the crude pyrolyzed liquid was collected in a trap maintained at the dry-ice temperature. The content of the object compound of vinyl ether $$CF_2=CFOCF_2CF(CF_3)O(CF_2)_3CO_2CH_3$$

was 68 g and the yield in the pyrolysis was 83%. The monomer of the vinyl ether was purified by a distillation as a fraction at 59° to 60° C./7mmHg.

What is claimed is:

1. A process for producing a fluorinated vinyl ether having an ester group which has the formula $$CF_2=CFOCF_2(CF(CF_3)OCF_2)_{n-1}(Rf)_mCO_2R$$

wherein n represents an integer of 1 to 5, m represents 0 or 1; Rf represents a $C_1$-$C_{10}$ bifunctional perfluoro group and R represents an alkyl group which comprises reacting a fluorinated acyl fluoride having an ester group which has the formula $$FOC(CF(CF_3)OCF_2)_n(Rf)_mCO_2R$$

with an alkali metal carbonate to produce an alkali metal salt of fluorinated carboxylic acid having an ester group which has the formula $$MOOC(CF(CF_3)OCF_2)_n(Rf)_mCO_2R$$

wherein M represents an alkali metal, and then, pyrolyzing the alkali metal salt of fluorinated carboxylic acid having an ester group.

2. A process according to claim 1 wherein the reaction of the fluorinated acyl fluoride having an ester group with an alkali metal carbonate is carried out at a reaction temperature in a range of $-30°$ C. to $+160°$ C.

3. A process according to claim 1 wherein the thermal decomposition of the alkali metal salt of fluorinated carboxylic acid having an ester group is carried out at a temperature in a range of 100° to 350° C.

4. A process according to claim 1 wherein the reaction of the fluorinated acyl fluoride having an ester group with an alkali metal carbonate is carried out in an inert organic solvent.

5. A process according to claim 1 wherein the thermal decomposition of the alkali metal salt of fluorinated carboxylic acid having an ester group is carried out in a polar organic solvent.

6. A process according to claim 1 wherein the reaction of the fluorinated acyl fluoride having an ester group with an alkali metal carbonate is carried out at a temperature in a range of 10° to 130° C. and the thermal decomposition of the alkali metal salt of fluorinated carboxylic acid having an ester group is carried out at a temperature in a range of 140° to 300° C.

7. A fluorinated vinyl ether containing an ester group which has the formula $$CF_2=CFOCF_2CF(CF_3)O(CF_2)_3CO_2C_2H_5.$$

8. A fluorinated vinyl ether containing an ester group which has the formula $$CF_2=CFOCF_2CF(CF_3)O(CF_2)_3CO_2CH_3.$$

* * * * *